United States Patent [19]
Shieh

[11] Patent Number: 6,054,039
[45] Date of Patent: Apr. 25, 2000

[54] DETERMINATION OF GLYCOPROTEIN AND GLYCOSYLATED HEMOGLOBIN IN BLOOD

[76] Inventor: Paul Shieh, 43513 Greenhills Way, Fremont, Calif. 94539

[21] Appl. No.: 08/914,283

[22] Filed: Aug. 18, 1997

[51] Int. Cl.[7] .................................................. G01N 27/26
[52] U.S. Cl. .......................... 205/792; 205/778; 204/403
[58] Field of Search ............................ 204/403; 205/792, 205/777.5, 778; 435/817

[56] References Cited

U.S. PATENT DOCUMENTS

| | | | |
|---|---|---|---|
| 5,366,868 | 11/1994 | Sakamoto | 435/10 |
| 5,437,999 | 8/1995 | Diebold et al. | 435/287.9 |
| 5,470,752 | 11/1995 | Burd et al. | 436/87 |
| 5,639,672 | 6/1997 | Burd et al. | 436/525 |
| 5,695,949 | 12/1997 | Galen et al. | 435/14 |

OTHER PUBLICATIONS

McFarland, et al, "Nonenzymatic Glucosylation of Serum Proteins in Diabetes Mellitus" Diabetes, vol. 28, Nov. 1979, 1011–1013.

Kennedy, et al, "Non–Enzymatically Glycosylated Serum Protein in Diabetes Mellitus: An Index of Short–Term Glycaemia" Diabetologia (1981) 21: 94–98.

Johnson, et al, "Fructosamine: a new approach to the estimation of serum glycosylprotein. An index of diabetic control" Clinica Chimica Acta, 127 (1982) 87–95 month unknown.

*Primary Examiner*—T. Tung
*Assistant Examiner*—Alex Noguerda
*Attorney, Agent, or Firm*—Marvin S. Aronoff

[57] ABSTRACT

A method of determining the concentration of glycoproteins and glycosylated hemoglobin in whole blood and whole blood components by means of an amperometric biosensor and an amperometric biosensor for this determination are provided. In one embodiment, whole blood is introduced into a version of an amperometric sensor having a component that removes erythrocytes. Redox mediators are used to obtain a current flow based on the oxidation of fructosamine derivatives that can be correlated with the concentration of glycosylated proteins in the fraction of the blood from which erythrocytes have been excluded. To obtain the concentration of glycosylated hemoglobin, whole blood is introduced into a version of the sensor which includes a component that produces lysis of the erythrocytes yielding a current flow proportional to the total quality of glycosylated proteins including glycosylated hemoglobin. The glycosyltaed hemoglobin concentration is obtained by subtracting the glycoprotein concentration in the absence of erythrocytes from the glycoprotein concentration of the lysed whole blood. The sensor generally comprises a sensing electrode having a first redox mediator dispersed in an electrically conductive medium such as an electrically conductive graphite formulation; a reference electrode such as a standard silver-silver chloride electrode; a reagent strip containing a pH buffer and a second redox mediator system in a gel medium; and a whole blood treatment component consisting of either a membrane or other means to filter erythrocytes from whole blood or a means to lyse erythrocytes. In a preferred form, that has high sensitivity, the sensing electrode and the reference electrode may be formed as coatings on separate non-conductive strips such as polyester film with these strips arranged so that they form "the bread" of a sandwich in which the electrode coatings are face-to-face and the reagent strip and the filtration or lysing component form the "filling" of the sandwich. The filtration or cell lysing component covers an opening in the reference electrode through which samples are introduced, and is superimposed on the reagent strip.

28 Claims, 3 Drawing Sheets

DETERMINATION OF GLYCOPROTEIN AND GLYCOSYLATED HEMOGLOBIN IN BLOOD

BACKGROUND OF THE INVENTION

This invention relates to a method for the rapid determination of glycosylated proteins in blood and a means for carrying out this method. The accurate assay of glycosylated protein levels in human blood and in particular, the quantity of glycoproteins to be found in the plasma and the fraction of glycosylated hemoglobin found in erythrocytes is important, particularly to those suffering from diabetes, because together they can yield a more accurate medium term and long term picture of an individual's glycemic state compared to blood glucose level which is subject to immediate large fluctuations due to factors such as food intake and physical activity among others. For example, such information is significant in determining the effects of therapy, changes in therapy and lifestyle changes on the extent to which the disease is under control in an individual. In addition, the initial diagnosis of diabetes can be made with more certainty when longer term indicia of an individual's glycemic state are taken into account.

According to information compiled by the National Diabetes Information Clearinghouse (NDIC), (NIH publication No. 96-3926, October, 1995), there were an estimated total of 16 million cases of diabetes in the United States in 1995 of which only about 8 million were diagnosed. The number of people suffering from insulin-dependent diabetes (IDDM) was estimated as high as 800,000, with noninsulin-dependent diabetes (NIDDM) estimated from about 7 to 7.5 million diagnosed cases. The estimated total medical costs directly attributable to diabetes were $45 billion and the estimated indirect costs due to disability, work loss and premature mortality were $47 billion in 1992. Diabetes was the seventh leading cause of death listed on United States death certificates in 1993, according to the National Center for Health Statistics. Based on the period 1990–1992, about 595,000 new cases of NIDDM and about 30,000 cases new cases of IDDM are diagnosed each year. Based on 1993 estimates about 100,000 children aged 19 or younger and 3.2 million adults aged 65 years or older were afflicted with this disease. People afflicted with diabetes also suffer from long term complications that strike them to a much greater degree than the general population. These include: heart disease, stroke, high blood pressure, blindness, kidney disease, nerve disease, amputations, dental disease.

From the above statistics it can be seen that the detection of diabetes and its control, is a health issue of major significance.

According to the NDIC treatment for diabetes emphasizes control of blood glucose through blood glucose monitoring, regular physical activity, meal planning, and attention to relevant medical and psychosocial factors. Oral medications and/or insulin injections are also required by many patients, for glucose control. The NDIC states (NIH publication No. 96-3626, October, 1995): "Treatment of diabetes is an ongoing process that is planned and regularly reassessed by the health care team, the person with diabetes, and his/her family."

A key element in the treatment of diabetes must therefore be the monitoring of the extent to which physiological indicia of diabetes have been brought within normal ranges or ranges considered appropriate to the individual by the health care team.

One such indication of the effectiveness of treatment is blood sugar level. Although commonly used, blood sugar level may not always give an accurate picture of the glycemic state of an individual as it is subject to variations produced by diet and physical activity.

Another approach to assessing the glycemic state of an individual is to determine the level of glycosylated proteins in blood serum and the level of glycosylated hemoglobin. Prolonged elevation of blood glucose in diabetes causes an increase in level of nonenzymatically glycosylated hemoglobin and glycosylated proteins. Glycosylated serum protein levels have been correlated with both fasting serum glucose and glycosylated hemoglobin levels. The degree of glycosylation of hemoglobin and serum proteins has been correlated with indices of glycemia. See for example: Bunn H P, Gabbay K H, Gallop P M, The glycosylation of hemoglobin: relevance to diabetes mellitus. *Science* 1978; 200:21–27; Dun P J, Cole R A, Soeldner J S et al. Temporal relationship of glycosylated hemoglobin concentration to glucose control in diabetics. *Diabetologia* 1979; 17:213–220; Paisey, R B, Macfarlane, D G Sherriff R J, Hartog M, Slade R R, White, D A, The relationship between blood glycosylated hemoglobin and home capillary blood glucose levels in diabetics. *Diabetologia* 1980; 19:31–34; McFarland K F, Catalano E W, Day J F, Thorpe S R, Baynes J W, Nonenzymatic glycosylation of serum proteins in diabetes mellitus. *Diabetes* 1979; 28: 1011–1014. Yue D K, Moris K S, Turtle J R, Glycosylation of plasma protein and its relation to glycosylated hemoglobin in diabetes, *Diabetes* 1980; 29:296–300, Dolhofer R, Wieland O H, Glycosylation of serum albumin in diabetes mellitus, *Diabetes* 1980; 29:417–422.

According to the literature in the field (see the above references) the following indicia can be used for the detection of diabetes in the first place and as measures of the degree to which it has been brought under control in an individual:

Blood serum glucose level: Under properly controlled circumstances this may give a good indication of the presence of the disease and the success of measures to control it in many individuals. The result of such assays in effect is a snap-shot of the glucose level at the time the test was taken. Generally the patient has fasted prior to the test in order to obtain a baseline glucose level. However, in some insulin-dependent diabetics large day-to-day variations in plasma glucose concentrations make this method ineffective.

Degree of non-enzymatic glycosylation of proteins found in blood plasma and serum. This is based on the non-enzymatic reaction of glucose with the available amino groups on proteins, such as albumin found in blood plasma. The chemistry of this process has been well worked out (see the above references): the glucose forms a Schiff base (or aldimine) with the amino group of the protein. The glucose moiety of the Schiff base then rearranges in a relatively slow step to form a fructosamine derivative of the protein (a glycoprotein). Thus, glycoprotein level does not reflect moment to moment changes in blood plasma (or serum) glucose levels, but is a longer term averaged reflection of blood glucose level. It has been established that plasma or serum fructosamine levels are a time averaged reflection of fasting blood glucose levels over the two to three week period prior to administration of the test (see L. Kennedy, et al, *Diabetologia*(1981) 21: 94–98). It is unaffected by time of day or previous food intake. An overnight fast is not required to yield valid results. Assays of plasma or serum for the fructosamine moiety are generally useful, for example, in assessing the glycemic state of diabetes patients where there has been a change in therapy.

Degree of glycosylation of hemoglobin: According to investigators in the field (e.g. McFarland, et al (*Diabetes*

1979; 28: 1011–1014)) levels of glycohemoglobins are indicative of the time-averaged blood glucose concentration over a period of several weeks due to the slow rate of glucosylation of hemoglobin and the 120 day average life span of erythrocytes. As with serum proteins, fructosamine derivatives are formed by reaction of available amino groups on hemoglobin with glucose by a non-enzymatic route (see for example Bunn, et al). This test is a measure of glycemic state for the period two to three months prior to the administration of the test. It is known in this field that poorly controlled diabetics may have two to four times the normal glycosylated hemoglobin level. Glycohemoglobin levels are also useful in assessing the level of control in insulin-dependent diabetics that have large day-to-day variations in plasma glucose concentrations.

Current procedures for the determination of glucosylated serum proteins include: a wet chemical method using thiobarbituric acid in which nonenzymatically bound glucose is released as 5-hydroxymethylfurfural and is assayed colorimetrically (see for example, McFarland, et al, Diabetes, vol 28, pp1012–1014, 1979); a wet chemical method utilizing the oxidation of fructosamine under alkaline conditions by nitroblue tetrazolium (NBT) to form a derivative that is assayed detected colorimetrically relative to a standard based on 1-deoxy-1-morpholinofructose (DMFr) (see Johnson, et al, Clinica Chemica Acta, vol. 27, pp 87–95, 1982); Burd et al, in U.S. Pat. No. 5,470,752 disclose a colorimetric method, based on a multilayered device for analyzing the concentration of fructosamine in a liquid sample that utilizes the ability of fructosamines to reduce an indicator such as NBT; Burd et al, in U.S. Pat. No. 5,639,672 disclose electrochemical methods for analysis of fructosamine in biological fluids, including the amperometric detection of the reduction of NBT by fructosamines.

Determination of glycosylated hemoglobins in whole blood, in practice often rely on fractionation procedures such as column chromatography, ion exchange resins and electrophoretic separation. The separation procedure may provide quantitative data on the level of glycosylated hemoglobin or colorimetric procedures may be used to obtain such data (see Isolab, Inc. publication on glycohemoglobin determination, revised Sep. 1, 1986, McFarland, et al, Diabetes, vol. 28, 1011–1014, 1979.). Work on separation of glycosylated hemoglobins from human blood led to the term Hb $A_1$ ($A_1$) to characterize all of the glycosylated hemoglobin fractions.

Currently, in the clinical laboratory setting, chromatographic and spectrophotometric instrumentation using either absorption or reflectance of light is generally used to assay blood glycosylated hemoglobin levels. Such instrumentation is expensive and relatively complex to use. The usual turnaround time in the clinical lab is at least 24 hours per analysis and the cost is relatively high. There is a need for a simple, rapid, highly sensitive, accurate and reproducible method to determine glycosylated hemoglobin levels and a means to carryout this method which can be easily miniaturized, inexpensively produced, and which is inexpensive to use. Such a method and means would be especially useful, convenient, and less painful to the patient when screening for and monitoring diabetes in the human if only a drop of blood was required for a reliable rest.

Both glycosylated hemoglobin levels which reflect the relatively long term glycemic state of a diabetic patient, and levels of glycosylated serum or plasma proteins, which reflect more recent, time averaged changes in the diabetic patient's glycemic state, resulting from changes in therapy or other factors, are important for the effective management of the diabetic patient. From the perspective of both the medical practitioner and the diabetic patient, it would be advantageous to have a simple, inexpensive method for determining glycosylated hemoglobin and levels of glycosylated serum or plasma proteins, that is convenient to use and that produces little or no pain and/or inconvenience for the patient. There is a need for a rapid, easy to use, inexpensive method to immediately obtain both the level of glycoproteins in plasma and the level of glycosylated hemoglobins in the red blood cells on a small, undiluted sample of whole blood.

In addition, for the foregoing reasons, there is a need for a device for the quantitative assay of glycoprotein, including glycosylated hemoglobin in blood and other fluids which is simple to use, is highly sensitive, accurate and reproducible and which can be easily miniaturized, inexpensively produced and inexpensively used to carry out such a method.

BRIEF DESCRIPTION OF THE INVENTION

The present invention is directed to meeting the foregoing needs by providing a simple and convenient method to assay all of the glycosylated proteins present in whole blood and whole blood components, including glycosylated hemoglobin present in red blood cells, as well as the glycosylated proteins in the plasma or serum fraction of blood, that is, the liquid fraction of whole blood, thus providing a basis for calculating the quantity of glycosylated hemoglobin in the red blood cells, and a means by which the method may be carried out in an efficient, accurate and economical manner. In this way, both a long term picture of the glycemic state of an individual based on glycosylated hemoglobin level and the shorter or medium term picture of the glycemic state of an individual based on glycosylated plasma or serum proteins can be obtained. Such information is crucial in assessing the effects of therapeutic or other changes on the glycemic state of an individual. It can be rapidly, accurately, efficiently and economically obtained with a minimum of inconvenience to the diabetic patient by using the method and sensor of the present invention.

In one embodiment, a test sample of whole blood is introduced into a version of an amperometric sensor that includes a whole blood treatment component that removes erythrocytes and other formed bodies from the whole blood. Redox mediators are used to obtain a current flow that can be correlated with the concentration of glycosylated proteins present. The current flow is based on the oxidation of fructosamine derivatives. It is well known in the art that fructosamine derivatives result from the non-enzymatic glycosylation of proteins found in blood. The resultant assay provides the concentration of glycosylated proteins in the fraction of the blood from which erythrocytes and other formed bodies have been excluded, that is, the plasma or serum.

To obtain the concentration of glycosylated hemoglobin, the test sample of whole blood is introduced into a version of the sensor that includes a whole blood treatment component that produces lysis (disruption of the cellular structure) of the erythrocytes rather than removing them. Redox mediators are used to obtain a current flow that can be correlated with the concentration of glycosylated proteins present. In this case the current flow will be proportional to the total quantity of glycosylated proteins in the blood including glycosylated hemoglobin. By subtracting the assay value for glycoproteins obtained where erythrocytes are essentially absent, from the assay value for glycoproteins obtained in the presence of lysed erythrocytes, the glycosylated hemoglobin level is obtained. The assay of lysed whole blood glycoproteins including glycosylated hemoglobin may be run prior to, or concurrent with, the assay of glycoproteins in the plasma or serum from whole blood.

The sensor of the present invention is an amperometric device that uses redox mediators to assay for glycosylated protein. It has high sensitivity and a wide range of linearity, thus enabling the direct and rapid measurement of glycosylated protein in biological fluids such as whole blood and whole blood components such as serum, plasma or other fractions without sample dilution. It may also be used on any other biological fluid that may contain glycosylated protein. Its high sensitivity enables glycosylated protein analyses to be run at potentials sufficiently low (e.g. below 200 mV) to avoid erroneous results produced by interfering substances.

The glyco biosensor generally comprises a sensing electrode having a first redox mediator dispersed in an electrically conductive medium such as an electrically conductive graphite formulation; a reference electrode such as a standard silver-silver chloride (Ag/AgCl) or calomel electrode; a reagent strip containing reagents and a second redox mediator system, in a gel medium; and a whole blood treatment component comprising either a membrane or other means to filter erythrocytes from whole blood or a means to lyse erythrocytes. In one embodiment, a component, typically a membrane, is incorporated to filter formed elements from whole blood, with the membrane covering at least a portion of the reagent strip to an extent sufficient to achieve filtration of samples introduced into the sensor. In another embodiment, a component, typically a membrane coated with a lysing agent, is incorporated to produce lysis of erythrocytes, with the coated membrane covering at least a portion of the reagent strip to an extent sufficient to achieve lysis of samples introduced into the sensor.

The electrically conductive medium of the sensing electrode contains a redox mediator such as dimethylferrocene (DMF), 7,7,8,8-Tetracyanoquinodimethane (TCNQ), Tetrathiafulvalene (TTF), Nickelocen (Nc), N-methylacridinium (NMA+), Tetrathiatetracene (TTT), N-methylphenazinium (NMP+) or mixtures thereof. The second redox mediator contained in the reagent strip may comprise various substances that can be reduced by fructosamine derivatives, such as: nitroblue tetrazolium (NBT), methylene blue (MB), hydrogen peroxide ($H_2O_2$), hydrazine, phenylhydrazine, ferredoxins, quinones, biooxidants, ferric chloride, hydrogen sulfide, sodium chlorate, sodium hypochlorate, barium diphenylamine sulfonate, 1,10-phenanthroline ferrous sulfate, nitro-1,10-phenanthroline ferrous sulfate, 2,2'-azino-di-[3-ethyl-benzthiazoline sulfonate] (ABTS), methyl violgen and mixtures thereof.

The glycosensor may be constructed in many physical forms. For example, the sensing and reference electrodes may comprise strips, arranged in a side-by-side configuration with the reagent strip forming a bridge that connects them and with the cell filtration component or lysing component superimposed on the reagent strip.

In another form, the sensing electrode and the reference electrode may be formed as a coating on separate non-conductive strips such as polyester film with these strips arranged so that they form "the bread" of a face to face sandwich with the reagent strip and the filtration or lysing component forming the "filling" of the sandwich. The filtration or cell lysing (that is, cell disrupting) component is arranged so that any sample that is introduced into the sensor must pass through the filtration or lysing component before reaching the reagent strip. The general configuration of such a face-to-face sandwich with respect to the electrodes and the reagent strip is disclosed in Guo et al. U.S. patent application Ser. No. 08/471,026, which is herein incorporated by reference.

One embodiment of the sensor of the present invention includes a membrane strip that is used to separate blood plasma from red blood cells. It was obtained by either modifying commercially available membranes, such as PrimeCare membrane (PC), Gelman Cytosep 1660, and Nucleopore membranes or by fabricating membranes and fibrous matrices with polymer treated glass fibers, for example, glass fibers of a thickness that increases from those designated as A to those designated as D that are coated with polyvinyl alcohol. A mixture of A and D fibers is herein designated (AVA/DVA).

In yet another form of the sensor, the membrane strip is modified to produce lysis of red blood cells (erythrocytes) that it contacts. Thus, whole blood that has passed through this membrane contains hemolyzed red blood cells. By assaying glycoprotein in plasma separated from red blood cells with one form of the membrane and also assaying whole blood containing lysed red blood cells produced by the second form of the membrane, the sensor can be used to detect both total glycoprotein and glycosylated hemoglobin.

The glycosensor of the present invention, has the advantages of being easily miniaturized, being easy to use, using small test samples without extensive sample preparation and producing accurate and reliable results rapidly.

DESCRIPTION OF THE PREFERRED EMBODIMENTS

In one embodiment of the method of the present invention, a test sample of whole blood is introduced into an amperometric sensor which includes a component that removes erythrocytes and other formed bodies from the whole blood. Redox mediators are used to obtain a current flow that can be correlated with the concentration of glycosylated proteins present. The current flow is based on the oxidation of fructosamine derivatives. A combination of redox mediators are used to obtain a current flow, at potentials that are low enough to avoid the oxidation of interfering impurities, such as ascorbate. It is well known in the art that fructosamine derivatives result from the non-enzymatic glycosylation of proteins found in blood. The resultant assay provides the concentration of glycosylated proteins, in terms of fructosamine concentration, in the fraction of the blood from which erythrocytes and other formed bodies have been excluded, that is, the plasma or serum.

It should be noted that the same chemical processes are involved in the reaction of free amino groups on hemoglobin with glucose as with serum or plasma proteins. That is, the resultant chemical grouping is a fructosamine that can be assayed by the same procedure as glycoproteins that are readily available in the serum or plasma. In one embodiment, the sensor of the present invention incorporates a membrane that disrupts the cellular structure of red blood cells making the fructosamine groups on hemoglobin accessible to assay.

To obtain the concentration of glycosylated hemoglobin, the test sample, generally ranging in size from a fraction of a drop to one or two drops of whole blood, is introduced into a version of the amperometric sensor that differs from the sensor used for assay of plasma glucosamine level by having a component that produces lysis (disruption of the cellular structure) of the erythrocytes, in place of the component that removes erythrocytes from whole blood. The resultant current is then correlated with the concentration of glycosylated proteins present. In this case, the current flow will be proportional to the total quantity of fructosamine which is an index of glycolsylated proteins in the blood, including glycated hemoglobin. By subtracting the fructosamine assay value obtained for glycoproteins where erythrocytes are essentially absent, from the assay value for glycoproteins as fructosamine obtained in the presence of lysed erythrocytes, the glycosylated hemoglobin level is obtained in terms of fructosamine concentration. The assay of lysed whole blood glycoproteins including glycosylated hemoglobin may be run prior to, or concurrent with, the assay of glycoproteins in the plasma or serum from whole blood, by using aliquots of the whole blood sample.

The sensor of the present invention is an amperometric device that uses redox mediators to assay for glycosylated protein. It has high sensitivity and a wide range of linearity, thus enabling the direct and rapid measurement of glycosylated protein in biological fluids such as serum, plasma or whole blood without sample dilution. Its high sensitivity enables glycosylated protein analyses to be run at potentials sufficiently low (e.g. below 200 mV) to avoid erroneous results produced by interfering substances.

Figure 1A:
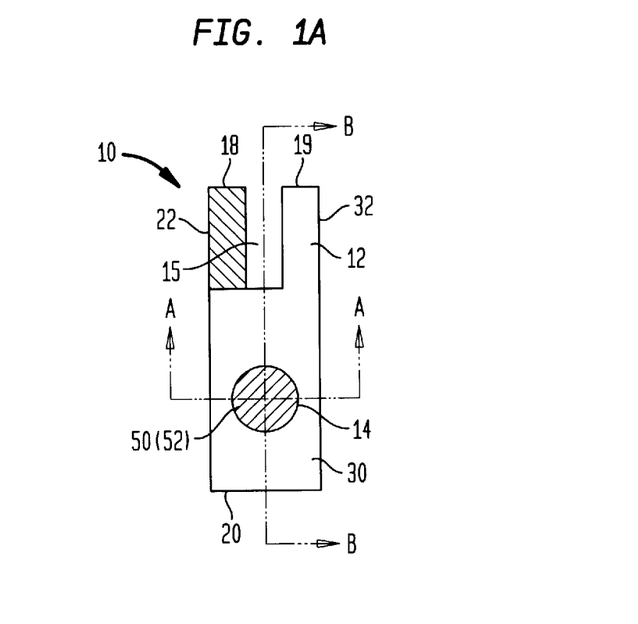
FIG. 1A is a top view of a face to face sandwich version of a Glyco Sensor of the present invention.
Figure 1B:
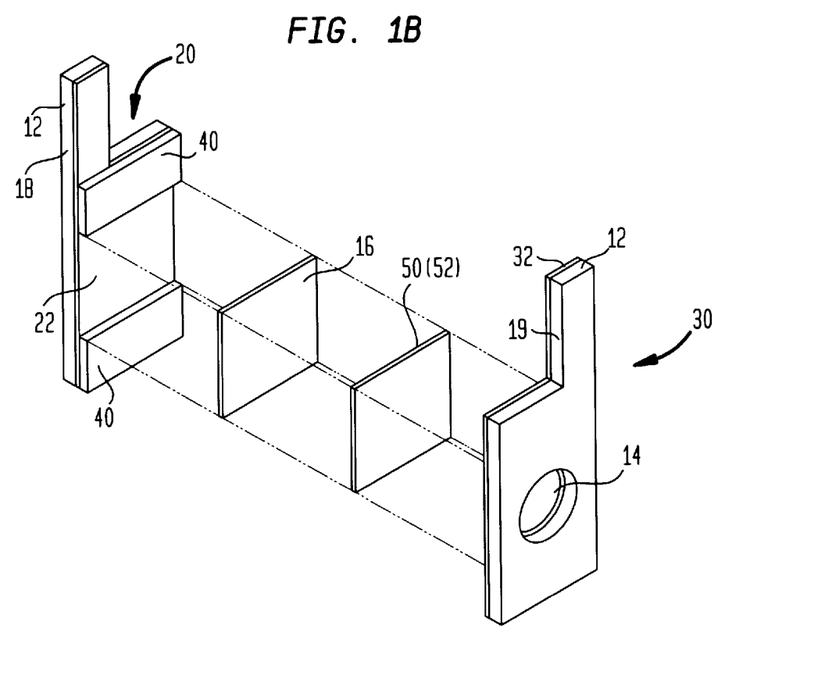
FIG. 1B is an exploded view of version of the Glyco Sensor of FIG. 1A.
Figure 1C:
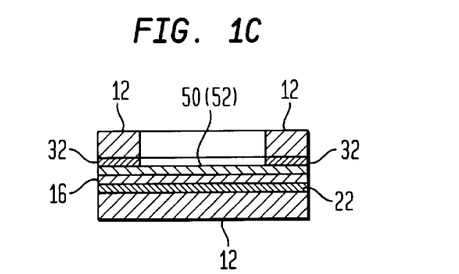
FIG. 1C is a cross-sectional view along the line A—A of FIG. 1A.
Figure 1D:
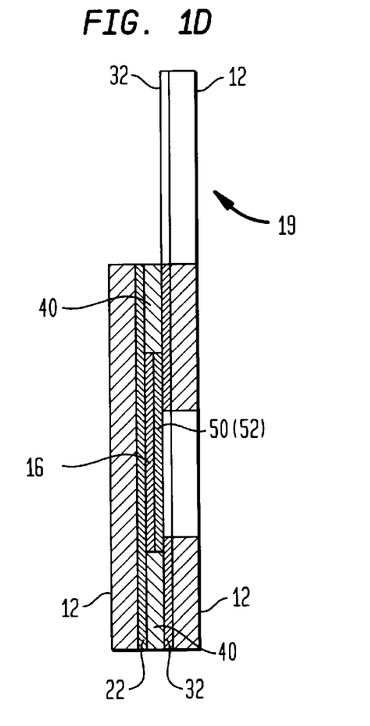
FIG. 1D is a cross-sectional view along the line B—B of FIG. 1A.
Figure 2:
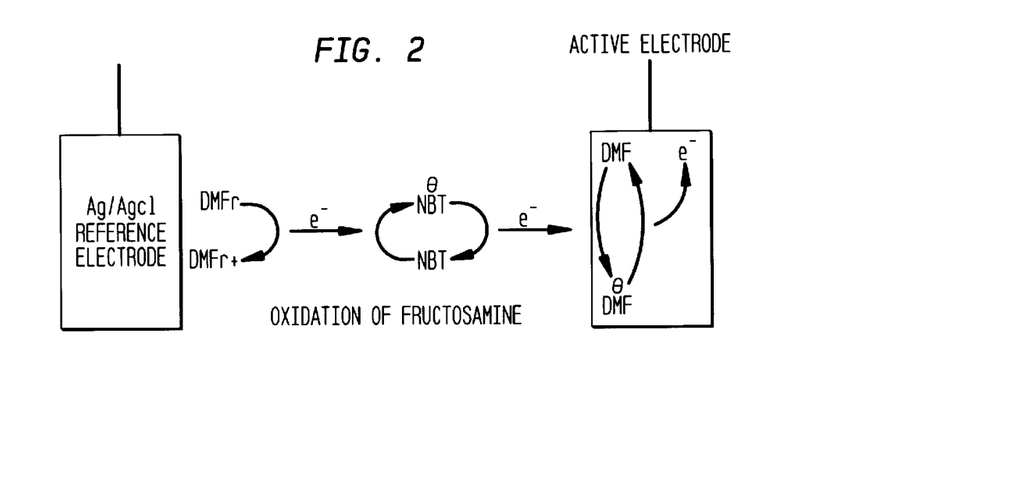
FIG. 2 depicts schematically the oxidation of fructosamine using a bi-mediator nonenzymatic system having DMF in the sensing electrode and NBT in the reagent strip.

A version of the glycoprotein sensor of the present invention that is preferred due to its high sensitivity is shown in FIGS. 1A–1D. FIG. 1A, is a top view, FIG. 1B is an exploded view of FIG. 1A, FIG. 1C is a cross-sectional view along line A—A and FIG. 1D is a cross-sectional view along line B—B of FIG. 1A of a glycosensor 10 which is an embodiment of the present invention. The glycosensor 10 generally comprises a sensing electrode 20, a reference electrode 30, reagent strip 16 and a whole blood treatment component which can be a cell filtration component 50 or a cell lysing component 52. In the version of the sensor depicted in FIGS. 1A–1D, the sensing electrode 20 has a conductive protrusion 18 and reference electrode 30 and has a conductive protrusion 19 separated by gap 15. Protrusions 18 and 19 serve as convenient points for rapid electrical connection. Reagent strip 16 and whole blood treatment component 50 or 52 are sandwiched between sensing electrode 20 and reference electrode 30, with whole blood treatment component 50 or 52 situated between reagent strip 16 and reference electrode 30. In the version of the sensor of FIG. 1A–D whole blood treatment component 50 or 52 may insulate reagent strip 16 from electrical contact with reference electrode 30 in the dry state, but electrical contact is made on introduction of a liquid sample. Opening 14 in reference electrode 30 is provided for introduction of a liquid sample. Whole blood treatment component 50 or 52 completely shields reagent strip 16 from immediate contact with liquid sample introduced through opening 14. The sample must first pass through whole blood treatment component 50 or 52 before contact is made with reagent strip 16. Electrical contact of reagent strip 16 with reference electrode 30 is then made via the liquid sample in this version of the sensor. The sandwich configuration may be optionally held together by clamps, tape and the like. Optionally, spacers 40 may be used to keep sensing electrode 20 and reference electrode 30 physically separated. Spacers 40 may comprise any non-conductive adhesive means, such as adhesives and double side adhesive tape.

Sensing electrode 20 comprises a non-conductive support member 12 for electrically conductive layer 22. The non-conductive support member may typically by any cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-conductive polymerics in the form of films or thin sheets are preferred as they may be readily cut to strips of suitable size. In practice non-conductive support 12 is a polymeric film or sheet. Any non-conductive polymeric film or sheet such as polyvinylchloride, polyester, polycarbonate, vinyl acetate copolymer, nylon, poly (1,4-butyleneterephthalate), cellulose propionate, ethylene/acrylic acid copolymer, polybutadiene, polyethylene, polypropylene, polyimide, acrylic film, polyurethane, polystyrene, and polyvinylfluoride may be used. Polyester film such as Mylar is preferred as it is readily available and easily handled.

Electrically conductive layer 22 of sensing electrode 20 comprises an electrically conductive layer containing a redox mediator. Electrically conductive layer 22 may be formed from any metallic or nonmetallic conductor having a physical state that can be blended with one or more redox mediators and deposited on non-conductive support layer 12 to form an electrically conductive layer. Formulations of electrically conductive graphite or carbon and polymeric substances are preferred. Formulations of electrically conductive carbon or graphite containing polymeric material such as the electrically conductive inks available from Ercon Inc. (Waltham, Mass.) are most preferred as they are readily available, can be uniformly spread on a non-conductive support member 12 to form a thin layer and can be easily blended with a redox mediator. Redox mediators which may be blended with electrically conductive formulations based on electrically conductive inks include dimethyl ferrocene (DMF), 7,7,8,8-tetracyanoquinodimethane (TCNQ), tetrathiafulvalene (TTF), Nicklocene (Nc), N-methylacridinium (NMA), Tetrathiatetracene (TTT), N-mthylphenazinium (NMP+), and mixtures thereof. DMF is preferred as it gives an easily detectable current change with change of glycoprotein concentration when used in conjunction with a second redox mediator in the reagent strip 16. The preferred concentration of the redox mediator in the electrically conductive layer 22, based on the total weight of the dry electrically conductive layer 22, ranges from about 0.2% to about 15% with concentration of about 0.5% to about 7% most preferred. Example 1a illustrates a process for making an embodiment of sensing electrode 20.

The term redox mediator is herein defined as a substance or substances that facilitates the flow of electrons in a reduction-oxidation reaction, so that the reaction may occur at a lower potential than when such substance or substances are absent.

Reference electrode 30 comprises a non-conductive support member 12 for electrically conductive layer 32. The non-conductive support member may typically be any cohesive non-conductor such as any non-conductive film or sheet forming polymeric material, ceramics, glass, paper, cardboard. The preferred thickness of the non-conductive support material is from about 5 mil to about 10 mil. Polymeric materials, particularly non-electrically conductive polymerics in the form of films or sheets are preferred as they may be readily cut to strips of suitable size. In practice, non-conductive support 12 is a polymeric film or sheet. Any non-conductive polymeric film or sheet such as those used for the sensing electrode may be used. Polyester film such as Mylar is preferred as it is readily available and easily handled.

Electrically conductive layer 32 of reference electrode 30 comprises a Ag/AgCl reference electrode prepared by coating a base support such as polyester film of PVC film with an electrically conductive formulation comprising Ag/Cl dispersed in a resin formulation, such as ERCON R-421 (DBE-60) Ag/AgCl and curing the coating for about one hour at about 70 C. Other forms of reference electrodes may be used such as the Ag/AgCl reference electrodes described in U.S. Pat. No. 5,401,377, which is herein incorporated by reference to the extent that it is pertinent, however, Ag/AgCl electrodes based on Ag/AgCl electrically conductive formulations which may be conveniently spread on a non-conductive base are preferred. Example 1b illustrates a process for making an embodiment of reference electrode 30.

Reagent Strip

Reagent strip 16 comprises a porous or fibrous water absorbent carrier impregnated with a reagent formulation. The carrier may be any water absorbent, porous medium including film, non-woven fabrics, felts, cellulosic papers, non-cellulosic papers, papers based on mixtures of cellulosic and non-cellulosic fibers or any water absorbent fibrous matrix, but commercially available cellulosic non-cellulosic papers such as Baxter S/P qualitative filter paper grade 360, Brawny paper (2-ply paper towel produced by James River Corp., Norwalk, Conn.), Leukosorb A and B polyester (Pall Corp., Glen Cove, N.Y.), Whatman filter paper Number 1,3,4 and 114, Teri-plus 4-ply and KimTowel (Kimberly-Clark, Roswell, Ga.) are preferred as they have an adequate degree of absorbency for the reagent formulation.

The reagent formulation contained in reagent strip 16 comprises a second compound or mixture of compounds that can function as a second redox mediator in addition to the first redox mediator which is contained in the sensing electrode, surfactants, and stabilizers. Compounds and mixtures of compounds which can function as the second redox mediator are compounds that can be reduced by fructosamine derivatives. Such compounds include nitroblue tetrazolium (NBT), methylene blue (MB), and thionin. NBT is preferred as it generally produces relatively large changes in current flow with changes of 1-deoxy, 1-morpholinofructose (DMFr), or glycoprotein concentration over a wide range. The weight of the second redox mediator in reagent strip 16 ranges from about 0.1 mg to about 5 mg per sensor with the preferred weight range from about 0.5 mg to about 1.0 mg per sensor.

The reagent strip formulation further comprises a buffering agent to maintain the pH between about 8 and about 12. Any buffering agent may be used that can maintain the pH in this range providing it does not interfere with the electron transfer reactions of the biosensor. Buffers such as $Na_2CO_3$ that can maintain the pH of the reagent strip between 10 and 11 are preferred when tetrazolium derivatives such as NBT are used.

The surfactants used in reagent strip 16 comprise Mega 8 (octanoyl-N-methylglucamide, Aldrich Chemical, Milwaukee, Wis.), cholic acid, salts of cholic acid, Triton X-100 (t-octylphenoxypolyethoxyethanol), polyethylene glycol, sodium lauryl sarcosinate and sodium lauryl sulfate used either separately or in combination. The preferred weight of surfactant ranges from about 0.1 mg to about 10 mg per sensor, with the most preferred weight ranging from about 0.5 mg to 1.0 mg per sensor.

Any water soluble or water dispersible aqueous thickening or gelling agent may be used as a stabilizer in the reagent strip 16 providing it does not interfere with chemical processes which occur during the glyco assay. Preferred stabilizers include sorbitol, gelatin, sucrose, bovine serum albumin, glutamate, L-arginine, mannitol, gum arabic, polypep, hydroxypropyl methylcellulose, and polyoxyethylene-2 cetyl ether used separately or in combination. The preferred weight of any stabilizer ranges from about 0.2 mg to about 1.0 mg per sensor. Example 1C illustrates a process for making an embodiment of reagent strip 16. Generally, when the reagent strip is wet, as by contact with water or a liquid sample, electrical contact is made between the sensing electrode and reference electrode in most embodiments of the sensor.

Filtering or Lysing Component

The sensor of the present invention includes a whole blood treatment component that is used to separate blood plasma from red blood cells. It was obtained either by use of commercially available membranes, such as PrimeCare membrane (Code S) (herein PC), Gelman Cytosep 1660, and Nucleopore membranes or by fabricating membranes or fibrous matrices. Polymer treated glass fibers, for example, glass fibers of a thickness that increases from those designated as A to those designated as D that are coated with polyvinyl alcohol may be used to create a fibrous matrix. A mixture of A and D fibers herein designated (AVA/DVA), can be used to create a suitable membrane by sintering or other processes known in the art. Membranes can be fabricated from polysulfones, polyamides, celluose derivatives, polyesters, polyvinylalcohol polymers and copolymers or any other film forming polymer or copolymer, alone or in combination, using processes well known in the art such as solution or melt casting. Methods known in the art such as inclusion of leachable materials in the polymer solution or melt can be used to create appropriately sized pores by leaching after membrane formation. Any membrane having a pore size sufficient to retain red blood cells while allowing the liquid fraction of whole blood to pass through can be used. The PrimeCare (Code S) polysulfone membrane is preferred.

The lysing component was prepared by treating the membranes used to separate blood plasma from red blood cells with a lysing agent. Any agent used in the art to cause disruption, hemolysis, or lysis of red blood cells may be used. Lysing agents which may be used include surfactants such as Mega 8 (Aldrich), Triton X (Sigma), lauryl sulfate salts, especially the sodium, ammonium and triethanolamine (TEA) salts, alpha olefin sulfonates, sulfosuccinate salts especially the sodium salt, sorbitol, lauric diethanolamide, lauryl dimethylamine oxide, lauryl amidopropyldimethylamine oxide, betaine, amidobetaine glycinate, sulfobetaine, stearyl dimethylbenzylammonium chloride, di($C_{12}$–$C_{18}$) dimethyl ammmonium chloride. The agent can be coated onto the membrane by an method used in the art for coating solutions onto films or membranes. For example, the lysing membrane may be prepared by dip coating an aqueous solution or dispersion of the lysing solution onto the membrane and then allowing to dry at ambient conditions overnight. The concentration of the lysing agent in solution will be dependent on the lysing agent, but generally is about 1% to about 5%, with about 1.5% to about 3% preferred. Surfactants such as Mega 8 are preferred lysing agents. A preferred substrate for preparation of the lysing component is the PrimeCare membrane (Code S).

The sensors of the present invention may be used at applied voltages of 600 mV and under, with applied voltages under 500 mV preferred and applied voltages under 300 mV more preferred. The most preferred applied voltages are under 200 mV as there is little or no oxidation of interfering substances in this range of applied voltages. The sandwich form of the glycoprotein biosensor described in the examples is the most preferred form as it can operate with high sensitivity at applied voltage under 200 mV.

The embodiments of the invention and their use are further illustrated by way of the following examples.

EXAMPLE 1A

This example illustrates the construction of a sensing electrode of the present invention. An equal amount by weight of graphite ink (Ercon G-448(I) Graphite, Ercon Inc) and electrically conductive graphite powder (Fisher Scientific Co, Pittsburg, Pa.) were mixed. This mixture was mixed with 10% DMF in toluene/alcohol(1/1) or DBE solvent to attain a mixture with a dynamic viscosity of about $2\times10^4$ poise at frequency of 1 radius/second. This mixture was laid down on a Mylar or PVC film base support and spread with a steel doctor knife having a gap of about 0.5 to about 6 mil to produce an evenly distributed thin layer. The graphite coating was cured at about 40° C. for 90 minutes. The electrode may also be fabricated by other methods known in the art such as stencil coating. Normally an approximately 5 mil stencil can be used.

EXAMPLE 1B

This example illustrates the general procedure for preparation of a reference electrode. A commercial polymer base Ag/AgCl ink (e.g. from Ercon, Inc.) was laid down on a Mylar base support and spread with a steel doctor knife with a gap ranging from 0.5 mil to 6 mil to obtain an evenly distributed thin layer. Typically the thickness of the wet material was about 1 mil. The Ag/AgCl coating was cured in an over at 70° C. for one hour. The electrode may also be fabricated by other methods known in the art such as stencil coating.

EXAMPLE 1C

A version of the reagent strip for the glycoprotein sensor was prepared as follows:

A solution of reagent strip components was prepared from about 0.04 gram NBT in about 1 ml ethanol/water(1:1), bout 0.06 gram mega 8, about 0.02 gram sorbitol and about 0.1 mg gelatin in about 3 ml, 0.1 M $Na_2CO_3$ buffer, pH at 10.8. Two pieces of approximately 4×8 cm Brawny paper were dip coated with the above solution. The paper was dried at about 150° F. for about 30 minutes.

EXAMPLE 1D

This example illustrates a general procedure for preparing a lysing membrane for the version of the sensor that is used to obtain an index of the total glycoprotein level of whole blood, including glycosylated hemoglobin, based on fructosamine content.

A cell lysing membrane was prepared by dipping a PrimeCare membrane, used to separate the formed bodies such as erythrocytes from whole blood, (see Example 2) into a 2% aqueous solution of a surfactant such as Mega 8 and allowing it to dry overnight.

EXAMPLE 1E

This example illustrates one method for the construction of a version of the glyco sensor having a sandwich configuration using the elements prepared in Example 1 A, B, C and D. A version of this configuration is shown in FIG. 1A through FIG. 1D. A hole 14 was punched out through a section of the reference electrode. Double sided adhesive tape (e.g. 3M #415 and 465; and ARcare® #7148, 7840 and 7841 (Adhesives Research Inc., Glen Rock, Pa.) was applied to the active surface of the reference electrode on both sides of the punched out hole A piece of lysing membrane prepared as in Example 1D was placed over the punched out hole 14 between the two pieces of double sided tape. A piece of reagent strip prepared in Example 1C was then superimposed on the lysing membrane. The sensing electrode was then placed over the reference electrode so that its active surface made contact with the reagent strip and pressed down, so that it adhered to the double faced tape, forming a sandwich, in which the active surfaces faced each other and the reagent strip and lysing membrane were sandwiched between the active surfaces of the sensing and reference electrodes. Sensors were of a scale to accommodate reagent strips and membrane components that were cut to a scale of 7 mm×12 mm. However, the sensors and their components may be made to any scale. In the version of the sensor used to obtain an index of glycoprotein level via fructosamine concentration in the plasma or serum from whole blood, an untreated PrimeCare membrane was used in place of the lysing membrane.

EXAMPLE 2

Figure 3:
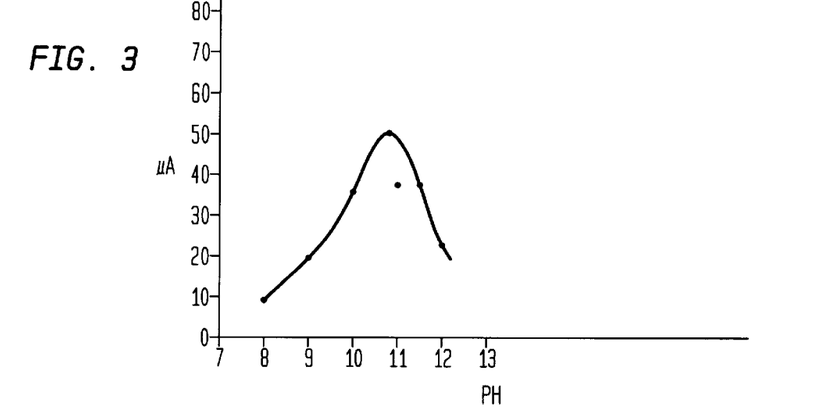
FIG. 3 is a graphical depiction of the response current generated by a glyco sensor one minute after the introduction of DMFr, as a function of pH.
Figure 4:
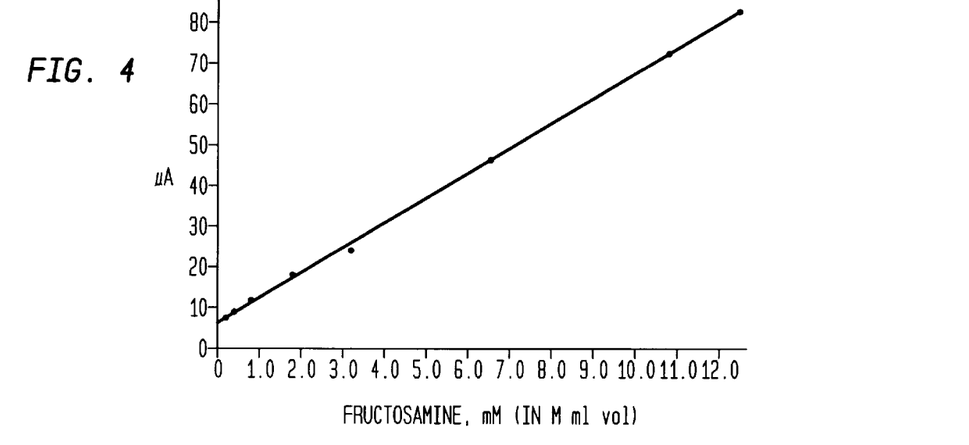
FIG. 4 is a calibration curve of an amperometric glycoprotein sensor showing the linear relationship of current response at 1 minute versus DMFr concentration.

A calibration curve based on DMFr was prepared as follows:

A solution of DMFr was prepared by dissolving 0.033 gram in 0.2 ml $Na_2CO_3$ buffer and then diluted to prepare various concentrations at $\frac{1}{10}$, $\frac{1}{100}$, $\frac{1}{1000}$, $\frac{1}{10000}$. 24 ul each of these DMFr solutions were added to the glycosensor prepared in Example 1D. The current generated under 174 mV applied voltage across the sensor was detected after 1 minute using an electrometer, FIG. 4 is a plot of the current response versus DMFr concentration. The calibration curve is a linear relationship between the current response and DMFr concentration in the range from 0 mM to 12.5 mM. The slope is 6.25 uA/mM. The magnitude of the current response was to some extent dependent on the wetting agent, stabilizer, and surfactant (e.g. mega 8), but especially on pH. FIG. 3 is a plot of current response versus pH. The optimum pH for the response is 10.8. It decreases at further increase in pH and decrease in pH.

Plasma Glycoprotein Measurement

Although DMFr (i.e. fructosamine) concentration can itself be used as an index of glycoprotein level, glycoprotein level is often expressed in the art relative to the weight of total serum protein, that is, in units of micromoles of glycoprotein per gram of serum protein ($\mu$M/g). Based on the work of Johnson, et al, *Clinica Chimica Acta*, 127 (1982) 87–95, which is herein incorporated by reference, a relationship was derived that can be used to convert DMFr concentration in mM/liter to $\mu$M/g of serum protein. This is given by linear relationship (A):

$$[\text{DMFr}] = 1.359 \times [\text{glycoprotein}] + 1.5 \quad (A)$$

Table 1 shows the glycoprotein level as $\mu$mol/g of serum protein for several unknown plasma samples as calculated from DMFr concentration measurements using relationship (A). These measurements were made with the version of the sensor used to obtain the DMFr calibration curve. Drops of human plasma obtained from whole blood separated by centrifugation were used for the plasma glycoprotein assay. For patients exhibiting a normal glycemic state, the glycoprotein level is below about 2 mM DMFr equivalent.

TABLE 1

| Plasma Source | Date | I,$\mu$A | DMFr mM | Glycoprotein $\mu$mol/g of protein |
|---|---|---|---|---|
| G | 7/23/96 | 14 | 1.25 | <0.07 |
| S | " | 12.5 | 0.95 | <0.07 |
| Gd | " | 12 | 0.90 | <0.07 |
| Gu | 8/26/96 | 18 | 1.85 | 0.26 |
| L | " | 16.4 | 1.61 | 0.08 |
| S | 10/7/96 | 17.5 | 1.8 | 0.22 |

EXAMPLE 3

Assay of Blood Plasma Glycoprotein, Glycosylated Proteins in Hemolyzed Whole Blood and Glycosylated Hemoglobin

A) Assay of Blood Plasma Glycoprotein

Assay of the glycoprotein level described in Example 2, was done on plasma derived from whole blood. In another method, a version of the sensor was used that incorporates a component to separate erythrocytes and other formed blood elements from whole blood, so that plasma glycoprotein level can be determined.

The version of the sensor incorporating a component to filter formed elements such as erythrocytes from whole blood used in the present example, employed a PrimeCare membrane (available from PrimeCare, Inc.). The membrane 50 was placed between the reference electrode 30 and the reagent strip 16 in a manner to completely cover the opening 14 in reference electrode 30. The membrane 50 used in the present example was of about the same shape and dimensions of the reagent strip 16 and was superimposed on it. However, in other versions, the membrane 50 may be of a size and dimension to completely cover the surface of reagent strip 16 exposed through opening 14, while still allowing contact of at least a portion of the electrically conductive layer 32 of reference electrode 30 with reagent strip 16, in the version of the sensor depicted in FIGS. 1A–1D.

Figure 5:
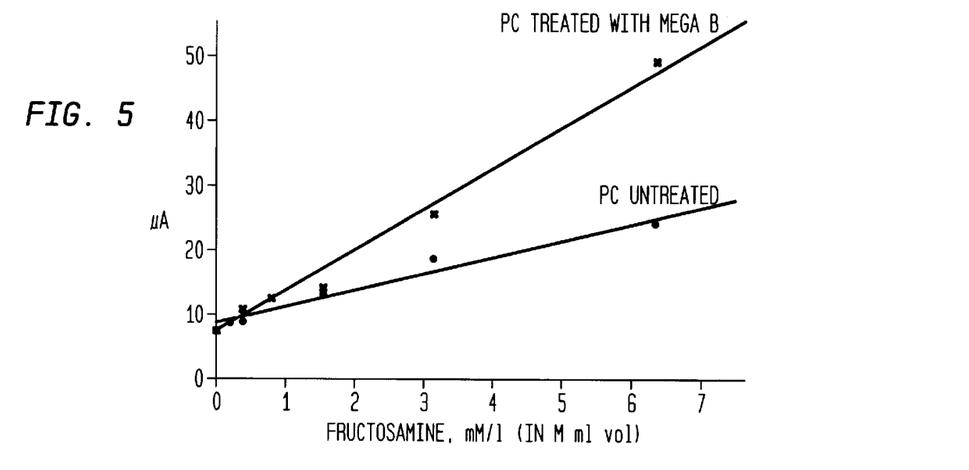
FIG. 5 depicts two calibration curves for amperometric glycoprotein sensors: in one case the sensor contains a membrane component to filter formed elements from whole blood; in the other case the sensor contains a membrane component that causes lysis of whole blood.

A calibration curve for a version of the sensor employing a PrimeCare (PC) membrane to filter erythrocytes and formed elements from whole blood, run at 174 mV applied potential, created by using the procedure described in Example 2, is shown in FIG. 5. The slope of the curve is 2.5 uA/mM DMFr. Calibration curves relating the current generated in the glycosensor to glycoprotein levels in whole blood, plasma or serum as well as glycohemoglobin levels may also be developed by any method known in the art. For example, calibration curves may be developed using samples of whole blood having known levels of glycoproteins and or glycohemoglobin. The values for glycoprotein concentration obtained with use of the filtration component are given in Table 2. These values are given in terms of DMFr (fructosamine) concentration.

B) Assay of Glycosylated Proteins in Hemolyzed Whole Blood and Glycosylated Hemoglobin For the determination of the total glycoprotein including plasma glycoprotein and glycosylated hemoglobin, a sensor is employed having a cell lysing component (i.e. a component which causes disruption of the cellular structure) in place of the separation membrane described in Example 2. The cell lysing component is typically prepared by chemical treatment of a membrane such as the PrimeCare membrane with an agent that produces lysis. A cell lysing component was prepared by dipping the PrimeCare membrane, used to separate the formed bodies such as erythrocytes from whole blood, in Example 2, into a 2% aqueous solution of a surfactant such as Mega 8 and allowing it to dry overnight. This component caused lysis of whole blood when it passed across the membrane. Other surfactants and agents known in the art to cause lysis of blood cells may be similarly used. The lysing component is incorporated into the sensor in the same place and in the same manner as described for the filtration component in Example 2.

A calibration curve for a version of the sensor employing a PrimeCare (PC) membrane chemically pretreated with Mega 8 to produce lysis, run at 174 mV applied potential, is given in FIG. 5. The slope is 6.25 uA/mM DMFr. Table 2 shows the total lysed whole blood glycoprotein determined for the same blood samples on which plasma glycoprotein was determined. These values are given in terms of DMFr (fructosamine) concentration. Glycosylated hemoglobin concentrations in terms of fructosamine concentration ($\Delta$DMFr mM) were calculated using equation (B):

$$(\Delta\text{DMFr mM}) = (\text{DMFrL mM}) - (\text{DMFrP mM}) \quad (B)$$

where DMFrL is the fructosamine concentration found for the lysed whole blood glycoproteins which includes glycosylated hemoglobin and plasma glycoproteins, and DMFrP is the fructosamine concentration found for plasma glycoproteins. These values are presented in Table 2.

TABLE 2

| Blood | Date | Plasma Glycoprotein | | Lysed Whole Blood | | Calculated Glycosylated Hemoglobin | |
|---|---|---|---|---|---|---|---|
| | | $\mu$A | DMFrP, mM | $\mu$A | DMFrL, mM | $\Delta$DMFr mM | $A_{1\%}$ |
| C | 10/5/96 | 10.2 | 0.5 | 22 | 2.40 | 1.9 | 5.56 |
| S | 10/5/96 | 10.9 | 0.9 | 22 | 2.40 | 1.5 | 5.00 |

TABLE 2-continued

| Blood | Date | Plasma Glycoprotein | | Lysed Whole Blood | | Calculated Glycosylated Hemoglobin | |
|---|---|---|---|---|---|---|---|
| | | DMFrP, $\mu$A | mM | DMFrL, $\mu$A | mM | $\Delta$DMFr mM | $A_1\%$ |
| G | 10/5/96 | 12.0 | 1.4 | 20 | 2.00 | 0.6 | 3.87 |
| N* (Normal Control) | | — | — | 15 | 1.25 | 1.25 | 4.68 |
| E* (Abnormal Control) | | — | — | 37 | 4.75 | 4.75 | 9.07 |

*Lysed red blood cells only.

By applying equation (A) to convert glycosylated protein concentration to units of $\mu$M/g of serum protein, it was found that for all the normal patient blood samples, blood plasma glycoprotein concentration stayed within 0.7 $\mu$mol/g protein.

$A_1\%$ in Table 2 represents the percentage of glycosylated hemoglobin with respect to the total hemoglobin in the erythrocytes. The general relationship between $A_1\%$ and glycosylated serum protein is well known in the art (see McFarland, et al, *Diabetes*, vol. 28, 1011–1014 (November, 1979), which is herein incorporated by reference).

Using the data of McFarland, equation (C) was derived to convert glycosylated hemoglobin expressed as $\mu$mol/g of serum protein into $A_1\%$.

$$A_1\% = 1.7 \times [\text{glycoprotein}] + 5 \quad (C)$$

The values for $\Delta$DMFr were converted to $\mu$M/g of serum protein using equation (A) and then $A_1\%$ was calculated from this value, as shown in Table 2.

It was found for all the normal patient blood samples that the $A_1\%$ glycosylated hemoglobin value was below 7–8%. The values obtained with normal and diabetic control samples show that the procedure and sensor of the current invention clearly distinguish between normal and diabetic glycosylated hemoglobin and glycoprotein levels and can be used to determine the glycemic state of patients.

The method and sensor of the present invention exhibit great sensitivity and have shown that glycosylated hemoglobin levels can, in some case, be slightly higher than blood plasma glycoprotein, while in other cases they can be slightly lower than blood plasma glycoprotein. The method and sensor of the present invention therefore conveniently enable the precise assessment of the intermediate and longer term glycemic state of a patient, showing the effects changes of therapy or lifestyle have produced in glycemic state against the background of the longer term glycemic state.

The advantages of the present invention include the ability to obtain an instantaneous direct measurement of the glycosylated protein level of whole blood, serum or plasma, and the level of glycosylated hemoglobin in the red blood cells, without sample treatment or dilution, thus enabling appraisal of the long term and intermediate term glycemic state of a patient. Another advantage is the ability to detect and assay glycoproteins on the spot: at home, in a physicians office or in a hospital room. Yet another advantage is the low cost and disposability of the biosensor. A further advantage is the ability of the sensor to function at low and negative applied constant voltage which greatly reduces the potential for interference. A still further advantage is the rapid response of the sensor enabling the assessment of a patient's intermediate term and longer term glycemic state in one (1) minute. Yet a further advantage is that the process of determining the glycemic state of a patient with the sensor of the present invention is simple, convenient and inexpensive making it possible for doctors and nurses or patients and members of the patient's family to perform the assay.

A still further advantage of the method and sensor of the present invention is that they enable the fast and convenient determination of glycosylated hemoglobin levels. Currently used methods require the separation of red blood cells from whole blood, usually via various types of chromatographic separation columns. The method and sensor of the current invention use whole blood without separation and are thus more convenient and more rapidly performed.

The sensor of the present invention may comprise part of a kit including electronic means to automatically calculate and or chart a patient's intermediate and longer term glycemic state. As will be apparent to those skilled in the art, the process of the present invention may be run by using both the version of the sensor having the filtering membrane and the version of the sensor having the lysing membrane together so that the glycoprotein level of plasma and lysed whole blood, are obtained simultaneously, thus enabling the instantaneous assessment of a patient's intermediate and long term glycemic state.

Although the present invention has been described in considerable detail with reference to certain preferred versions thereof, other versions are possible. For example, other versions of the glyco biosensor are possible as is its use in conjunction with instrumentation such as devices for automatically assaying large numbers of samples. Versions of the glyco biosensor of the present invention may also comprise a portion of an analytical kit. Therefore, the spirit and scope of the appended claims should not be limited to the description of the preferred versions contained herein.

What is claimed is:

1. An amperometric sensor for assaying the concentration of a fructosamine moiety contained in a biological fluid in the presence of interfering oxidizable substances also contained in the fluid, comprising:

a sensing electrode, the sensing electrode comprising;
    a non-conductive support member strip,
        with the non-conductive support member strip coated with an electrically conductive layer, with the electrically conductive layer containing;
            a first redox mediator; and
a reference electrode comprising;
    a non-conductive support member strip, with the support member strip coated with an electrically conductive formulation comprising Ag/AgCl dispersed in a resin formulation, and with the reference electrode having an opening; and
a reagent strip, the reagent strip comprising;
    a water absorbent carrier, the water absorbent carrier impregnated with a mixture comprising;
        a second redox mediator that can be reduced by a fructosamine derivative,
        at least one surfactant,
        at least one stabilizer,
        a buffering agent to maintain a pH from about 8 to about 12; and
    a whole blood treatment component selected from the group consisting of;
        an erythrocyte filtration component and an erythrocyte lysing component;
with the electrically conducting layer of the sensing electrode and the electrically conductive formulation of the reference electrode facing each other; and with the reagent strip superimposed on and in physical contact with the electrically conducting layer of the sensing electrode, and with the whole blood treatment component superimposed on and in physical contact with the reagent strip; and with the reference electrode superimposed on the whole blood treatment component so that the electrically conductive formulation coating the reference electrode is in physical contact with the whole blood treatment component; and with the whole blood treatment component completely covering the opening in the reference electrode; so that the sensing electrode and the reagent strip and the whole blood treatment component and the reference electrode form a sandwich.

2. The sensor of claim 1 in which the first redox mediator contained in the electrically conductive layer of the sensing electrode is selected from the group consisting of dimethyl ferrocene, 7,7,8,8-tetracyanoquinodimethane, tetrathiafulvalene, nicklocene, N-methylacridinium, tetrathiatetracene, N-methylphenazinium, and mixtures thereof.

3. The sensor of claim 2 in which the second redox mediator impregnated in the reagent strip is selected from the group consisting of nitroblue tetrazolium, methylene blue, thionin and mixtures thereof.

4. The sensor of claim 3 in which the erythrocyte filtration component comprises a component selected from the group of components consisting of membranes and fibrous matrices having a pore size sufficient to retain erythrocytes while allowing passage of a liquid fraction of whole blood.

5. The sensor of claim 4 in which the erythrocyte lysing component comprises a filtration component further comprising a coating selected from the group consisting of octanoyl-N-methylglucamide surfactant, Triton X surfactant, lauryl sulfate salts, alpha olefin sulfonates, sulfosuccinate salts, sorbitol, lauric diethanolamide, lauryl dimethylamine oxide, lauryl amidopropyldimethylamine oxide, betaine, amidobetaine glycinate, sulfobetaine, stearyl dimethylbenzylammonium chloride, di($C_{12}$–$C_{18}$) dimethyl ammonium chloride and mixtures thereof.

6. The sensor of claim 5 in which the erythrocyte filtration component and the erythrocyte lysing component are comprised of materials selected from the group consisting of polysulfones, polyamides, celluose derivatives, polyesters, polyvinylalcohol polymers, glass fibers and mixtures thereof.

7. The sensor of claim 6 in which the erythrocyte filtration component comprises a polysulfone membrane and the erythrocyte lysing component comprises a polysulfone membrane further comprising a coating of octanoyl-N-methylglucamide surfactant.

8. The sensor of claim 7 in which the electrically conductive layer of the sensing electrode comprises a formulation containing an electrically conductive material selected from the group consisting of electrically conductive carbon or electrically conductive graphite, and the first redox mediator contained in the electrically conductive layer of the sensing electrode is dimethyl ferrocene and the second redox mediator impregnated in the reagent strip is nitroblue tetrazolium and the reagent strip further comprises, stabilizers, surfactants and a buffer to maintain a pH of about 10 to a pH of about 11.

9. The sensor of claim 8 in which the non-conductive support member strip of the sensing electrode comprises a non-conductive polymeric film and the non-conductive support member strip of the reference electrode comprises a non-conductive polymeric film.

10. The sensor of claim 11 in which the sensing electrode further comprises a conductive protrusion and the reference electrode further comprises a conductive protrusion, with the protrusions having a gap separating them, with the protrusions providing points of contact for electrical connection.

11. A method for the amperometric determination of the concentration of fructosamine derivatives contained in a sample of whole blood or fractions thereof, in the presence of interfering oxidizable substances also contained in the sample, comprising the steps of:

providing an amperometric biosensor for fructosamine derivatives having high sensitivity at low applied potentials, the biosensor comprising;
    a sensing electrode, with the sensing electrode comprising;
        a non-conductive support strip, with the non-conductive support strip coated with an electrically conductive layer, with the electrically conductive layer containing a first redox mediator, and
    a reference electrode, with the reference electrode comprising;
        a non-conductive support strip, with the non-conductive support strip coated with an electrically conductive formulation comprising Ag/AgCl dispersed in a resin formulation, and with the reference electrode having an opening; and
    a reagent strip, with the reagent strip comprising;
        a water absorbent carrier, with the water absorbent carrier containing a second redox mediator comprising at least one compound that can be reduced by a fructosamine derivative, and a buffering agent to maintain a pH from about 8 to about 12; and
    a whole blood treatment component with the whole blood treatment component comprising;
        a component selected from the group consisting of an erythrocyte filtration component and an erythrocyte lysing component,
with the electrically conducting layer of the sensing electrode and the electrically conductive formulation of the reference electrode facing each other; and with the reagent strip superimposed on and in physical contact with the electrically conducting layer of the sensing electrode, and with the whole blood treatment component superimposed on and in physical contact with the reagent strip; and with the reference electrode superimposed on the whole blood treatment component so that the electrically conductive formulation coating the reference electrode is in physical contact with the whole blood treatment component and with the whole blood treatment component completely covering the opening in the reference electrode; so that the sensing electrode and the reagent strip and the whole blood treatment component and the reference electrode form a sandwich;

contacting the whole blood treatment component of the biosensor with an aliquot of a whole blood sample and, maintaining a potential of 500 mV or less across the sensing electrode and the reference electrode and, measuring the current passing between the sensing electrode and the reference electrode and, comparing the current measured to a calibration curve of the concentration of a fructosamine versus current for the biosensor, whereby the concentration of the fructosamine is substantially precisely determined in the presence of the interfering substances.

12. The method of claim 11 in which the sensing electrode comprises a non-conductive polymeric film coated with an electrically conductive layer comprising an electrically conductive carbon or graphite formulation containing the first redox mediator, with the first redox mediator selected from the group consisting of dimethyl ferrocene, 7,7,8,8-tetracyanoquinodimethane, tetrathiafulvalene, nicklocene, N-methylacridinium, tetrathiatetracene, N-methylphenazinium, and mixtures thereof.

13. The method of claim 12 in which the second redox mediator is selected from the group consisting of nitroblue tetrazolium, methylene blue, thionin and mixtures thereof.

14. The method of claim 13 in which the erythrocyte filtration component comprises a component selected from the group of components consisting of membranes and fibrous matrices having a pore size sufficient to retain erythrocytes while allowing passage of a liquid fraction of the whole blood.

15. The method of claim 14 in which the erythrocyte lysing component comprises a filtration component further comprising a coating selected from the group consisting of octanoyl-N-methylglucamide, Triton X surfactant, lauryl sulfate salts, alpha olefin sulfonates, sulfosuccinate salts, sorbitol, lauric diethanolamide, lauryl dimethylamine oxide, lauryl amidopropyldimethylamine oxide, betaine, amidobetaine glycinate, sulfobetaine, stearyl dimethylbenzylammonium chloride, di($C_{12}$–$C_{18}$) dimethyl ammonium chloride and mixtures thereof.

16. The method of claim 15 in which the erythrocyte filtration component and the erythrocyte lysing component are comprised of materials selected from the group consisting of polysulfones, polyamides, celluose derivatives, polyesters, polyvinylalcohol polymers, glass fibers and mixtures thereof.

17. The method of claim 16 in which the erythrocyte filtration component comprises a polysulfone membrane and the erythrocyte lysing component comprises a polysulfone membrane further comprising a coating of octanoyl-N-methylglucamide surfactant.

18. The method of claim 17 in which the first redox mediator contained in the electrically conductive layer of the sensing electrode comprises dimethyl ferrocene and the second redox mediator contained in the reagent strip comprises nitroblue tetrazolium and the reagent strip further comprises, stabilizers, surfactants and sodium carbonate buffer.

19. The method of claim 11 in which the potential maintained across the sensing electrode and the reference electrode does not exceed 200 mV.

20. A method for the amperometric determination of the concentration of glycosylated hemoglobin contained in a sample of whole blood in the presence of interfering oxidizable substances also contained in the whole blood sample comprising the steps of:

providing a first and a second amperometric biosensor for fructosamine derivatives, with the first biosensor having a whole blood treatment component comprising an erythrocyte filtration component and the second biosensor having a whole blood treatment component comprising an erythrocyte lysing component, with each biosensor further comprising;

a sensing electrode, with the sensing electrode comprising;

a non-conductive support strip, with the non-conductive support strip coated with an electrically conductive layer, with the electrically conductive layer containing a first redox mediator;

a reference electrode, with the reference electrode comprising;

a non-conductive support strip, with the non-conductive support strip coated with an electrically conductive formulation comprising Ag and AgCl dispersed in a resin formulation, and with the reference electrode having an opening; and a reagent strip, with the reagent strip comprising;

a water absorbent carrier, with the water absorbent carrier containing a second redox mediator comprising at least one compound that can be reduced by a fructosamine derivative, and a buffering agent to maintain a pH from about 8 to about 12;

with the electrically conductive layer of the sensing electrode and the electrically conductive formulation of the reference electrode facing each other; and with the reagent strip superimposed on and in physical contact with the electrically conducting layer of the sensing electrode, and with the whole blood treatment component superimposed on and in physical contact with the reagent strip; and with the reference electrode superimposed on the whole blood treatment component so that the electrically conductive formulation coating the reference electrode is in physical contact with the whole blood treatment component and with the whole blood treatment component completely covering the opening in the reference electrode; so that the sensing electrode and the reagent strip and the whole blood treatment component and the reference electrode form a sandwich; and introducing an aliquot of a whole blood sample into each biosensor; and maintaining a potential of 500 mv or less across the sensing electrode and the reference electrode of each biosensor and, measuring the current passing between the sensing electrode and the reference electrode of each biosensor, and comparing the current measured for each biosensor to a calibration curve of the concentration of a fructosamine derivative versus current corresponding to each biosensor to determine the corresponding concentration of the fructosamine derivative measured by each biosensor, and subtracting the concentration of fructosamine derivative determined with the first biosensor having the erythrocyte filtration component from the concentration of fructosamine derivative determined with the second biosensor having the erythrocyte lysing component to obtain the concentration of glycosylated hemoglobin in the whole blood.

21. The method of claim 20 in which the sensing electrode of each biosensor further comprises a non-conductive polymeric film coated with an electrically conductive layer comprising an electrically conductive carbon or graphite formulation containing the first redox mediator, with the first redox mediator selected from the group consisting of dimethyl ferrocene, 7,7,8,8-tetracyanoquinodimethane, tetrathiafulvalene, nicklocene, N-methylacridinium, tetrathiatetracene, N-methylphenazinium, and mixtures thereof.

22. The method of claim 21 in which the second redox mediator of each biosensor is selected from the group consisting of nitroblue tetrazolium, methylene blue, thionin and mixtures thereof.

23. The method of claim 22 in which the erythrocyte filtration component comprises a component selected from the group of components consisting of membranes and fibrous matrices having a pore size sufficient to retain erythrocytes while allowing passage of the liquid fraction of the whole blood.

24. The method of claim 23 in which the erythrocyte lysing component comprises a filtration component further comprising a coating selected from the group consisting of octanoyl-N-methylglucamide, Triton X surfactant, lauryl sulfate salts, alpha olefin sulfonates, sulfosuccinate salts, sorbitol, lauric diethanolamide, lauryl dimethylamine oxide, lauryl amidopropyldimethylamine oxide, betaine, amidobetaine glycinate, sulfobetaine, stearyl dimethylbenzylammonium chloride, di($C_{12}$–$C_{18}$) dimethyl ammonium chloride and mixtures thereof.

25. The method of claim 24 in which the erythrocyte filtration component and the erythrocyte lysing component are comprised of materials selected from the group consisting of polysulfones, polyamides, celluose derivatives, polyesters, polyvinylalcohol polymers, glass fibers and mixtures thereof.

26. The method of claim 25 in which the erythrocyte filtration component comprises a polysulfone membrane and the erythrocyte lysing component comprises a polysulfone membrane further comprising a coating of octanoyl-N-methylglucamide.

27. The method of claim 26 in which the electrically conductive layer of the sensing electrode of each biosensor comprises electrically conductive graphite or carbon and the first redox mediator contained in the electrically conductive layer of each biosensor comprises dimethyl ferrocene and the second redox mediator contained in the reagent strip of each biosensor comprises nitroblue tetrazolium and each strip further comprises, stabilizers, surfactants and sodium carbonate buffer.

28. The method of claim 20 in which the potential maintained across the sensing electrode and the reference electrode does not exceed 200 mV.

* * * * *